US010745353B2

(12) United States Patent
Sahl et al.

(10) Patent No.: US 10,745,353 B2
(45) Date of Patent: Aug. 18, 2020

(54) POLYMER ADDITIVE AND A METHOD FOR THE PRODUCTION THEREOF

(71) Applicant: CLARIANT PLASTICS & COATINGS LTD, Muttenz (CH)

(72) Inventors: Mike Sahl, Bad Camberg (DE); Eduard Zeisberger, Neusaess (DE); Matthias Zaeh, Gersthofen (DE); Ottmar Schacker, Gersthofen (DE); Pascal Steffanut, Village-Neuf (FR)

(73) Assignee: Clariant Plastics & Coatings Ltd, Muttenz (CH)

( * ) Notice: Subject to any disclaimer, the term of this patent is extended or adjusted under 35 U.S.C. 154(b) by 44 days.

(21) Appl. No.: 15/739,458

(22) PCT Filed: May 31, 2016

(86) PCT No.: PCT/EP2016/062301
§ 371 (c)(1),
(2) Date: Dec. 22, 2017

(87) PCT Pub. No.: WO2017/005413
PCT Pub. Date: Jan. 12, 2017

(65) Prior Publication Data
US 2018/0194727 A1 Jul. 12, 2018

(30) Foreign Application Priority Data

Jul. 3, 2015 (DE) .......................... 10 2015 212 508

(51) Int. Cl.
| | | |
|---|---|---|
| C07D 211/58 | (2006.01) | |
| C08K 5/00 | (2006.01) | |
| C08K 5/3435 | (2006.01) | |
| C07C 233/79 | (2006.01) | |
| C08L 23/08 | (2006.01) | |
| C08L 29/04 | (2006.01) | |
| C08L 67/00 | (2006.01) | |
| C08L 77/00 | (2006.01) | |
| G01N 23/20 | (2018.01) | |

(52) U.S. Cl.
CPC .......... *C07D 211/58* (2013.01); *C07C 233/79* (2013.01); *C08K 5/005* (2013.01); *C08K 5/3435* (2013.01); *C08L 23/0846* (2013.01); *C08L 29/04* (2013.01); *C08L 67/00* (2013.01); *C08L 77/00* (2013.01); *C08L 2201/08* (2013.01); *G01N 23/20075* (2013.01)

(58) Field of Classification Search
CPC ..................................................... C07D 211/58
See application file for complete search history.

(56) References Cited

U.S. PATENT DOCUMENTS

| | | | |
|---|---|---|---|
| 5,241,067 A | 8/1993 | Myers | |
| 10,336,699 B2 * | 7/2019 | Zhang | .................. C07D 211/58 |

FOREIGN PATENT DOCUMENTS

| | | | |
|---|---|---|---|
| CN | 103030588 A | | 4/2013 |
| CN | 103508938 A | | 1/2014 |
| CN | 103554009 A | | 2/2014 |
| CN | 104557676 A | * | 4/2015 |
| CN | 104974075 A | * | 10/2015 ........... C07D 211/58 |
| CN | 106905225 A | * | 6/2017 |
| EP | 97/043335 A1 | | 11/1997 |
| WO | 2004/016591 A1 | | 2/2004 |

OTHER PUBLICATIONS

Machine translated ENglish language equivalent of CN-104974075-A (2015, 8 pages).*
Machine translated ENglish language equivalent of CN-106905225-A (2017, 5 pages).*
Machine translated ENglish language equivalent of CN-104557676-A (2015, 4 pages).*
International Search Report for PCT/EP2016/062301, dated Jul. 18, 2016.
Written Opinion for PCT/EP2016/062301, dated Jul. 18, 2016.
Caira, M.R., "Crystalline Polymorphism of Organic Compounds", Topics in Current Chemistry, 163-208 (1998).

* cited by examiner

*Primary Examiner* — Brieann R Johnston
(74) *Attorney, Agent, or Firm* — Morgan, Lewis & Bockius LLP

(57) ABSTRACT

The invention relates to a compound of formula (I), characterised by the characteristic signals in the X-ray diffraction powder pattern measured with Cu Kalpha radiation (0.154 nm) at a 2-theta angle of 15.0 and 22.7 with a high intensity, and of 5.0, 11.3, 18.9, 20.8, 21.6 and 23.6 with a medium intensity, as well as to a method for producing the compound of formula (I) by reacting at least one isophthalic acid diester of formula (II) where R1 and R2 are the same or different and stand for an aliphatic group, with two equivalents 4-amino-2,2,6,6-tetramethylpiperidine, in the presence of at least one catalyst from the group of metal alcoholates and at a reaction temperature of between 50 and 150° C.

15 Claims, No Drawings

POLYMER ADDITIVE AND A METHOD FOR THE PRODUCTION THEREOF

The present invention relates to the production of the polymer additive of the formula (I) in a crystal morphology which was unknown to date for the polymer additive for formula (I), and to a preparation process therefor.

The polymer additive of the formula (I):

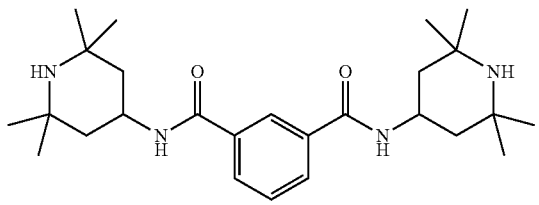

(I)

was described for the first time in WO 97/43335 and has since been used as an effective stabilizer against the harmful effect of heat and light in polyamides in particular. This compound is typically prepared under Schotten-Baumann conditions according to reaction equation (1) of WO 2004/016591:

Reaction equation (1):

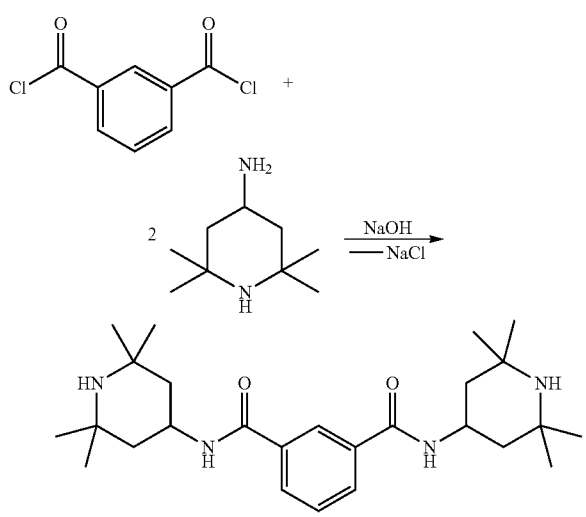

This is done using mixtures of water and isopropanol as solvent.

The crystal structure of the polymer additive of the formula (I) prepared according to reaction equation (1) is characterized in the x-ray diffractogram by six peaks of high intensity at a 2-theta angle of 5.7, 14.9, 15.2, 17.8, 22.7, 23.7; four peaks of moderate intensity at a 2-theta angle of 16.9, 20.2, 21.8, 26.8; and further peaks of low intensity at a 2-theta angle of 9.3, 10.5, 11.3, 12.9, 14.1, 16.5, 19.7, 24.9, 28.5, 30.7, 31.5, 32.0, 33.0, 34.0, 35.9, 37.6, 39.5, 40.6, 41.1, 43.1, 45.3, 47.2, 48.1, 59.0. This known crystal phase is referred to hereinafter as alpha phase.

The alpha phase is difficult to handle on the industrial scale, since the powder isolated from the synthesis is dusty and has poor free flow and a low bulk density, which necessitates costly and inconvenient compaction.

SUMMARY OF THE INVENTION

It was an object of the present invention to provide a practicable process by which it is possible to prepare the polymer additive of the formula (I) with improved physical properties compared to the prior art.

A further object of the invention was that of providing a process for producing the polymer additive of the formula (I), which has the feature of avoiding the use of toxic and corrosive acid chlorides, the formation of halide salts that necessitate costly removal and disposal, and costly cooling. Moreover, the process is to assure a reliable and reproducible reaction regime.

It has been found that, surprisingly, this object is achieved by a process which is based on amidation of isophthalic diesters with 4-amino-2,2,6,6-tetramethylpiperidine and which is conducted using a catalyst from the group of the metal alkoxides (reaction equation (2)).

Reaction equation (2):

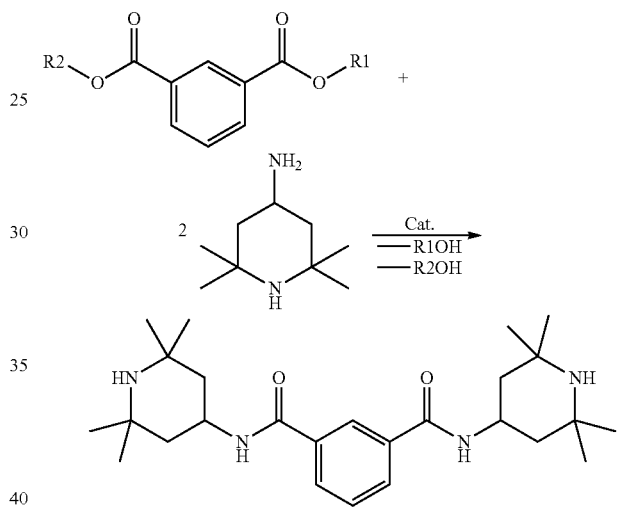

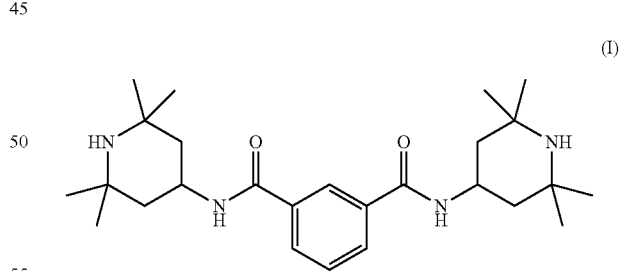

The invention provides a process for preparing the compound of the formula (I)

(I)

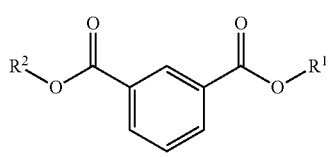

by reacting at least one isophthalic diester of the formula (II)

(II)

in which $R^1$ and $R^2$ are the same or different and are an aliphatic radical with 2 equivalents of 4-amino-2,2,6,6-tetramethylpiperidine, in the presence of at least one catalyst from the group of the metal alkoxides, at a reaction temperature between 50 and 150° C.

In a preferred form, $R^1$ and $R^2$ are each an aliphatic radical having 1 to 20, preferably 1 to 6 and more preferably 1 to 4 carbon atoms. The aliphatic radical may be linear, branched or cyclic. It may be saturated or unsaturated, preferably saturated. Suitable aliphatic radicals are, for example: methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, sec-hexyl, n-heptyl, n-octyl, 2-ethylhexyl, n-nonyl, n-decyl, cyclopropyl, cyclobutyl, cyclopentyl, cyclohexyl, cycloheptyl, cyclooctyl, cyclononyl, cyclodecyl. Particular preference is given to the methyl, ethyl, n-propyl, isopropyl and n-butyl radicals.

Particular preference is given to isophthalic diesters in which the $R^1$ and $R^2$ radicals are each methyl, ethyl, n-propyl, isopropyl or n-butyl.

Catalysts in the context of the present invention are alkoxides of the formula (VI) and/or (VII)

(VI)

(VII)

where the radicals $R^{14}$ and $R^{15}$ are each the same or different;

$R^{13}$, $R^{14}$ and $R^{15}$ are aliphatic radicals each having 1 to 20 carbon atoms, for example methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, sec-hexyl, n-heptyl, n-octyl, 2-ethylhexyl, n-nonyl, n-decyl, or $C_3$-$C_{12}$-cycloalkyl radicals, for example cyclopropyl, cyclobutyl, cyclopentyl, cyclohexyl, cycloheptyl, cyclooctyl, cyclononyl, cyclodecyl, cycloundecyl and cyclododecyl.

Preference is given to methyl, ethyl and tert-butyl.

X represents alkali metals, for example lithium, sodium, potassium, rubidium and cesium. Preference is given to lithium, sodium and potassium;

Y represents alkaline earth metals, for example beryllium, magnesium, calcium, strontium and barium. Preference is given to magnesium and calcium.

Preferred catalysts are, for example, sodium methoxide, potassium methoxide, lithium methoxide, sodium ethoxide, potassium ethoxide, lithium ethoxide, sodium n-propoxide, potassium n-propoxide, sodium isopropoxide, potassium isopropoxide, sodium butoxide, potassium butoxide, sodium isobutoxide, potassium isobutoxide, sodium sec-butoxide, potassium sec-butoxide, sodium tert-amoxide, sodium amoxide, potassium amoxide, potassium tert-butoxide.

The catalyst is appropriately added to the reaction mixture in amounts of 1 to 20 mol %, preferably 2 to 15 mol %, especially 3 to 12 mol %, based on the isophthalic diester.

In order to prevent losses of yield and purity, it is also appropriate that the catalyst on addition to the reaction mixture is fully dissolved in an alcohol, for example in the alcohol from which it has been prepared, preferably in 1 to 4 times the amount of alcohol, based on the mass of the catalyst.

In a preferred embodiment of the process of the invention (process variant a), the reaction is conducted in a solvent-free manner and in a reaction apparatus from the group of the mixers, kneaders and extruders. In these reaction apparatuses, liquid and solid mixtures of liquid and solid materials can be mixed using shear forces.

In the context of the present invention, a solvent-free process is understood to mean a process that contains only such a small amount, if any, of an organic solvent, for example alcohols, aliphatic or aromatic hydrocarbons, that the reaction product does not go into solution under the given reaction temperatures and precipitates directly out of the reaction mixture in solid form.

In process variant a), it is appropriate that the isophthalic diester is mixed with about two equivalents of 4-amino-2,2,6,6-tetramethylpiperidine in the reaction apparatus; in other words, neither the isophthalic diester nor the amine is used in excess. The amount of alcohol introduced into the reaction mixture by the catalyst, relative to the mass of the co-reactants, is so small that the reaction of the invention can be described as solvent-free. In general, the alcohol introduced by the catalyst is removed from the reaction mixture, for example by distillation, together with the alcohol formed in the reaction.

The desired reaction product of the formula (I) is solid at the reaction temperature of the invention (melting point about 272° C.) and is obtained in solid form without having passed through the molten state beforehand.

The reaction apparatus used is appropriately a device with which liquid and solid mixtures of liquid and solid substances can be mixed using shear forces. In a static housing, the movements of the reaction mixture are brought about by internal mechanical stirring or mixing devices. Rotation of the housing and static mechanical internals are also possible, but not preferred. Addition of grinding bodies such as balls of steel or of various ceramics is possible, but unnecessary. The reaction apparatus can be operated in batchwise operation or in continuous operation.

The reaction apparatus in process variant a) is appropriately a kneader or mixer, preferably equipped with sigma blades, masticator blades, plowshares, Becker blades or throwing paddles. As an alternative, the reaction apparatus may also be an extruder, for example a single-spindle or twin-spindle screw kneader.

Useful apparatuses include:
planetary mixers equipped with mixing tools such as, for example, cross beams, a vane type mixing unit, a helical type mixing unit or a comb blade stirring unit,
horizontally or vertically operating blade type kneaders equipped with mixing tools, for example sigma blades, masticator blades, plowshares, Becker blades or throwing paddles,
single-spindle screw kneaders,
twin-spindle screw kneaders equipped with corotating or contrarotating screw bands,
band screw mixers equipped with a twin band screw,
cone mixers with single or double helix design,
tumble mixers,
freefall mixers whose drum walls are optionally equipped with mixing tools, for example spirals, paddles or blades,
horizontal or vertical forced mixers equipped with mixing tools, for example sigma blades, masticator blades, plowshares, Becker blades or throwing paddles, in combination with a cutting rotor,
preferably horizontally operating blade type kneaders equipped with mixing tools, or combinations of mixing tools, such as, for example, sigma blades, masticator blades, plowshares, Becker blades or throwing paddles, further preferably twin-spindle screw kneaders with counterrotating screw bands, further preferably horizontal forced mixers equipped with mixing tools or combinations of mixing tools such as, sigma blades, masticator blades, plowshares, Becker blades or throwing paddles, in combination with a cutting rotor installed in the drum;

more preferably horizontal forced mixers operating at a Froude number between 0.1 and 6, preferably between 0.25 and 5 and more preferably between 0.4 and 4, and equipped with mixing tools, or combinations of mixing tools, such as, for example, sigma blades, masticator blades, plowshares, Becker blades or throwing paddles in combination with a cutting rotor installed in the drum.

The agitation state especially of solid mixtures in the case of horizontal forced mixers can be characterized via the dimensionless Froude number Fr. The following equation is applicable here:

$$Fr=v^2/r\cdot g$$

with v=circumferential speed of mixing elements r=radius of mixing drum g=acceleration due to gravity.

In a specific embodiment of process variant a), 1 equivalent of isophthalic diester and 2 equivalents of 4-amino-2,2,6,6-tetramethylpiperidine are mixed with one another at a temperature between 40 and 150° C., preferably 45 to 120° C., especially 50 to 110° C., appropriately under protective gas, to give a homogeneous (monophasic) mixture without solvent and preferably in a horizontal forced mixer that works at a Froude number between 0.1 and 6, preferably between 0.25 and 5, more preferably between 0.4 and 4, and is equipped with mixing tools or combinations of mixing tools, for example sigma blades, masticator blades, plowshares, Becker blades or throwing paddles, optionally in combination with a cutting rotor installed in a drum. Particularly preferred protective gases are nitrogen and argon. After formation of the homogeneous mixture, the reaction mixture is adjusted by closed-loop control to the desired temperature, which is between 50 and 150° C., preferably 80 to 120° C., especially 90 to 110° C. Subsequently, the catalyst is added to the homogeneous reaction mixture in amounts of 1 to 20 mol %, preferably 2 to 15 mol, especially 3 to 12 mol %, based on the isophthalic diester. After the addition of the catalyst, the reaction mixture is mixed by the stirring and mixing devices of the reaction apparatus, appropriately for a period of 10 to 400 minutes, preferably 30 to 300 minutes, especially 45 to 120 minutes, and the alcohol formed is removed from the reaction mixture, preferably by distillation, at a pressure of 0.1 to 1013 mbar, preferably 0.2 to 500 mbar, especially 0.3 to 250 mbar. After the reaction apparatus has been ventilated, preferably with protective gas, the reaction mixture is cooled down to room temperature. The polymer additive of the formula (I) is obtained here in solid form in high purity and high yields.

In a further embodiment of the process of the invention (process variant b), the isophthalic diester is dissolved in an excess of 4-amino-2,2,6,6-tetramethylpiperidine. The molar ratio between isophthalic diester and 4-amino-2,2,6,6-tetramethylpiperidine in this case is 1:3.9 mol to 1:27.5 mol, preferably 1:6.25 mol to 1:18 mol, more preferably 1:8.6 mol to 1:13.35 mol. Subsequently, the catalyst is added, preferably at a temperature between 50 and 80° C., especially between 60 and 70° C., and the reaction mixture is heated, preferably to a temperature between 80 and 150° C., especially between 85 and 130° C. Optionally, the alcohol formed can be removed from the reaction mixture by distillation during the reaction. The polymer additive of the formula (I) precipitates out of the reaction mixture and can be filtered off. Process variant b) is appropriately conducted in a solvent-free manner like variant a).

In a further embodiment of the process of the invention (process variant c), the isophthalic diester is dissolved with about two equivalents of 4-amino-2,2,6,6-tetramethylpiperidine and a lipophilic liquid hydrocarbon or a mixture of such hydrocarbons, for example hexane, heptane, octane, dodecane, petroleum ether, Shellsol, white spirit or Exxsol, preferably at a temperature between 20 and 40° C., then the catalyst is added, preferably at a temperature between 50 and 80° C., especially between 60 and 70° C. The mass ratio between solvents and reactants is between 90%:10% by weight and 50%:50% by weight, preferably 85%:15% by weight and 60%:40% by weight, more preferably 80%:20% by weight and 70%:30% by weight. Subsequently, the reaction mixture is heated, preferably to a temperature between 80 and 150° C., especially between 85 and 110° C. Optionally, the alcohol formed can be removed from the reaction mixture by distillation. The polymer additive of the formula (I) precipitates out of the reaction mixture and can be filtered off.

One of the advantages of the process of the invention over the prior art is that the polymer additive of the formula (I) can be synthesised in a solvent-free manner (variants a and b), without using excesses of reactant (variants a and c), in high purity and virtually quantitative yields, and without additional purification steps. Furthermore, the process of the invention avoids the formation of wastewater contaminated with halide salts or possibly reactant, the proper disposal of which has a significant effect on the overall costs of the production of the polymer additive of the formula (I). The avoidance of halide salts in the form of secondary condensation products also rules out the contamination of the polymer additive of the formula (I) therewith, which can in turn be of crucial significance for the commercial proliferation thereof.

The particularly preferred variant is process variant a).

Furthermore, it has been found that, surprisingly, the process of the invention, especially in process variants a), b) and c), affords the compound of the formula (I) in a novel crystal polymorph, called the beta phase. The beta phase is characterized in the x-ray diffractogram by two peaks of high intensity at a 2-theta angle of 15.0, 22.7; six peaks of moderate intensity at a 2-theta angle of 5.0, 11.3, 18.9, 20.8, 21.6, 23.6; and further numerous peaks of low intensity, for example at a 2-theta angle of 7.1, 10.1, 12.2, 16.0, 16.8, 17.8, 18.2, 19.7, 24.8, 25.6, 26.7, 27.2, 28.5, 29.3, 30.5, 32.5, 33.5, 34.1, 36.2, 37.3, 38.4, 40.6, 41.3, 44.3, 46.5. Peaks of high intensity are those having a relative intensity of more than 50%. Peaks of moderate intensity are those having a relative intensity of 35% to 50%. Peaks below 35% are described as being of low intensity.

The invention further provides a compound of the formula (I) obtainable by the above-described process of the invention.

The invention further provides a compound of the formula (I) in the beta phase,

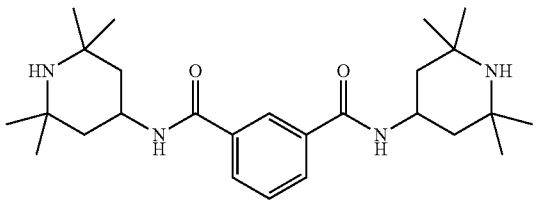

(I)

characterized by the characteristic signals in the x-ray powder diagram, measured with Cu $K_{alpha}$ radiation (0.154 nm) at a 2-theta angle of 15.0 and 22.7 having a high intensity and of 5.0, 11.3, 18.9, 20.8, 21.6 and 23.6 having a moderate intensity.

The compound of the formula (I) in the beta phase is surprisingly characterized by advantageous physical properties, for example low dust formation, better flowability and higher bulk density compared to the alpha phase known to date. This makes compaction significantly simpler or superfluous. The bulk density of the beta phase, obtained from the process of the invention, is in the range from 0.40 to 0.65 $g/cm^3$, preferably from 0.45 and 0.60 $g/cm^3$.

The bulk density can be determined according to DIN 53468, EN ISO 60 at room temperature (23-25° C.), for example with the aid of a Karg Fluometer ADP.

The compound of the formula (I) in the beta phase is usable as polymer additive, especially for stabilization, especially of polymers, preferably polyamides, EVOH and polyesters, e.g. PET, against light and heat, and for improving the oxygen barrier properties, especially of EVOH.

EXAMPLES

The products were analyzed by means of $^1$H NMR spectroscopy at 400 MHz in DMSO-$d_6$ and HPLC under isocratic conditions. The continuous phase used in the HPLC was an acetonitrile/water mixture (70% by weight/30% by weight). The stationary phase used was an RP-18 column.

The x-ray diffractograms have been measured by means of Cu K alpha radiation (0.154 nm) at a temperature of 20° C. on a PANalytical X'Pert Pro MPD PW 3040/00 with an X'Celerator detector.

Preparation of N,N'-bis-(2,2,6,6-tetramethylpiperidin-4-yl)isophthalamide in the β phase (m.p.: 272° C.):

Example 1

Process Variant a

In a horizontal forced mixer that works at a Froude number of 2.16 and has been equipped with plowshares, a distillation column and a protective gas connection, 2.5 mol of dimethyl isophthalate (m.p. 64-66° C.) and 5 mol of 4-amino-2,2,6,6-tetramethylpiperidine (in liquid form at room temperature) are homogenized with one another at a temperature of 60° C. under nitrogen until a monophasic liquid mixture forms. After the addition of 59.4 g of a sodium methoxide solution (25% by weight in methanol), the reaction mixture is mixed at 110° C. for a duration of 90 minutes. The alcohol from the catalyst formulation and the alcohol formed during the reaction are removed by distillation from the forced mixer. After the solid had been discharged and dried to constant weight, 1088.4 g (mass yield: 98.5%) of a white powder were isolated.

The bulk density of the product was about 0.53 $g/cm^3$.

HPLC analysis of the white solid gave the following composition:

| Substance | mol % |
| --- | --- |
| Product | 99.7 |
| Monoamide | 0.1 |
| 4-Amino-2,2,6,6-tetramethylpiperidine | 0.1 |
| Dimethyl isophthalate | 0.1 |

In the x-ray diffractogram, the following signals were identified for the product:

| 2 theta | d/angström | Absolute intensity | Relative intensity/% |
| --- | --- | --- | --- |
| 4.99 | 17.69 | 10429.00 | 42.28 |
| 7.12 | 12.42 | 8059.00 | 32.67 |
| 10.11 | 8.75 | 3057.00 | 12.39 |
| 11.27 | 7.85 | 11217.00 | 45.47 |
| 12.19 | 7.26 | 4110.00 | 16.66 |
| 14.97 | 5.92 | 24667.00 | 100.00 |
| 16.00 | 5.54 | 5368.00 | 21.76 |
| 16.83 | 5.27 | 3289.00 | 13.33 |
| 17.76 | 4.99 | 6477.00 | 26.26 |
| 18.22 | 4.87 | 7616.00 | 30.88 |
| 18.88 | 4.70 | 9158.00 | 37.13 |
| 19.68 | 4.51 | 7802.00 | 31.63 |
| 20.82 | 4.27 | 11672.00 | 47.32 |
| 21.57 | 4.12 | 11646.00 | 47.21 |
| 22.67 | 3.92 | 17291.00 | 70.10 |
| 23.56 | 3.78 | 9127.00 | 37.00 |
| 24.78 | 3.59 | 5763.00 | 23.36 |
| 25.60 | 3.48 | 4740.00 | 19.22 |
| 26.70 | 3.34 | 5518.00 | 22.37 |
| 27.21 | 3.28 | 5428.00 | 22.01 |
| 28.52 | 3.13 | 4108.00 | 16.65 |
| 29.29 | 3.05 | 4554.00 | 18.46 |
| 30.48 | 2.93 | 5588.00 | 22.65 |
| 32.45 | 2.76 | 3628.00 | 14.71 |
| 33.45 | 2.68 | 4144.00 | 16.80 |
| 34.08 | 2.63 | 4649.00 | 18.85 |
| 36.22 | 2.48 | 4644.00 | 18.83 |
| 37.33 | 2.41 | 4463.00 | 18.09 |
| 38.37 | 2.35 | 4433.00 | 17.97 |
| 40.61 | 2.22 | 5763.00 | 23.36 |
| 41.32 | 2.18 | 6110.00 | 24.77 |
| 44.33 | 2.04 | 6077.00 | 24.64 |
| 46.49 | 1.95 | 5742.00 | 23.28 |

Example 2

Process Variant a

In a horizontal forced mixer that works at a Froude number of 2.16 and has been equipped with plowshares, a distillation column and a protective gas connection, 2.5 mol of dibutyl isophthalate (in liquid form at room temperature) and 5 mol of 4-amino-2,2,6,6-tetramethylpiperidine (in liquid form at room temperature) are homogenized with one another at a temperature of 60° C. under nitrogen. After the addition of 59.4 g of a sodium methoxide solution (25% by weight in methanol), the reaction mixture is mixed at 130° C. for a duration of 180 minutes. In addition, a reduced pressure of 50 mbar is applied. The alcohol from the catalyst formulation and the alcohol formed during the reaction are removed by distillation from the forced mixer. After the solid had been discharged and dried to constant weight, 1075.6 g (mass yield: 97.3%) of a white powder were isolated.

The bulk density of the product was about 0.53 g/cm$^3$.

HPLC analysis of the white solid gave the following composition:

| Substance | mol % |
|---|---|
| Product | 99.7 |
| Monoamide | 0.1 |
| 4-Amino-2,2,6,6-tetramethylpiperidine | 0.1 |
| Dimethyl isophthalate | 0.1 |

In the x-ray diffractogram, the same characteristic signals as reported in example 1 were observed for the product.

Example 3

Process Variant b

In a multineck flask with reflux condenser, precision glass stirrer, N$_2$ inlet and internal thermometer, at a temperature of 30° C., 1 mol of dimethyl isophthalate is dissolved in 8.6 mol of 4-amino-2,2,6,6-tetramethylpiperidine. Subsequently, the reaction mixture is heated to a temperature of 50° C., and 23.76 g of sodium methoxide, dissolved in methanol (25% by weight), are added. After the addition of the catalyst, the reaction mixture is heated to a temperature of 90° C. for 4 hours. The polymer additive of the formula (I) precipitates out of the reaction mixture during this time and, after 4 hours have elapsed, is filtered off with suction at room temperature. After drying to constant weight, it was possible to isolate 415 g of a white solid (94% yield).

HPLC analysis of the white solid gave the following composition:

| Substance | mol % |
|---|---|
| Product | >99.7 |
| Monoamide | <0.1 |
| 4-Amino-2,2,6,6-tetramethylpiperidine | <0.1 |
| Dimethyl isophthalate | <0.1 |

In the x-ray diffractogram, the same characteristic signals as reported in example 1 were observed for the product. The bulk density of the product was 0.54 g/cm$^3$.

Example 4

Process Variant c

In a 4 L multineck flask with reflux condenser, precision glass stirrer, N$_2$ inlet and internal thermometer, at a temperature of 40° C., 1 mol of dimethyl isophthalate and 2 mol of 4-amino-2,2,6,6-tetramethylpiperidine are dissolved in 1700 g of n-heptane. Subsequently, the reaction mixture is heated to a temperature of 50° C., and 23.76 g of sodium methoxide, dissolved in methanol (25% by weight), are added. After the addition of the catalyst, the reaction mixture is heated to a temperature of 90° C. for 6 hours. The polymer additive of the formula (I) precipitates out of the reaction mixture during this time and, after 6 hours have elapsed, is filtered off with suction at room temperature. After drying to constant weight, it was possible to isolate 424 g of a white solid (96% yield).

HPLC analysis of the white solid gave the following composition:

| Substance | mol % |
|---|---|
| Product | >99.5 |
| Monoamide | 0.2 |
| 4-Amino-2,2,6,6-tetramethylpiperidine | 0.2 |
| Dimethyl isophthalate | <0.1 |

In the x-ray diffractogram, the same characteristic signals as reported in example 1 were observed for the product. The bulk density of the product was 0.57 g/cm$^3$.

Example 5

Comparative Example

Preparation of N,N'-bis(2,2,6,6-tetramethylpiperidin-4-yl)isophthalamide in the α phase according to DE 60315329 T2 (m.p.: 272° C.):

A reaction flask is charged with 0.95 mol (150.5 g) of 4-amino-2,2,6,6-tetramethylpiperidine and 1.07 mol (85.2 g) of 50% by weight aqueous NaOH solution in 470 g of isopropanol and 260 g of demineralized water. While stirring, 0.5 mol (102.1 g) of isophthaloyl chloride is added. Subsequently, the reaction mixture is heated to a temperature of 100° C., and the solids go completely into solution. 2 liquid phases are formed, of which the organic phase is removed and admixed with water, and the alcohol is distilled off. After cooling, the product is filtered off, washed with water and dried to constant weight. The yield of the reaction product is 200.0 g (95% of the theoretical value).

The bulk density of the product is about 0.20 g/cm$^3$.

In the x-ray diffractogram, the following signals were identified:

| 2 theta | d/angström | Absolute intensity | Relative intensity/% |
|---|---|---|---|
| 5.66 | 15.62 | 31473.00 | 100.00 |
| 9.33 | 9.48 | 7325.00 | 23.27 |
| 10.54 | 8.40 | 3475.00 | 11.04 |
| 11.28 | 7.84 | 7997.00 | 25.41 |
| 12.87 | 6.88 | 5399.00 | 17.15 |
| 14.14 | 6.26 | 5640.00 | 17.92 |
| 14.89 | 5.95 | 25649.00 | 81.50 |
| 15.16 | 5.84 | 28327.00 | 90.00 |
| 16.50 | 5.37 | 7164.00 | 22.76 |
| 16.91 | 5.24 | 13596.00 | 43.20 |
| 17.78 | 4.99 | 16524.00 | 52.50 |
| 19.67 | 4.51 | 10433.00 | 33.15 |
| 20.19 | 4.40 | 12160.00 | 38.64 |
| 21.79 | 4.08 | 11911.00 | 37.85 |
| 22.66 | 3.92 | 21629.00 | 68.72 |
| 23.68 | 3.76 | 17097.00 | 54.32 |
| 24.87 | 3.58 | 7694.00 | 24.45 |
| 26.77 | 3.33 | 10583.00 | 33.63 |
| 28.45 | 3.14 | 6061.00 | 19.26 |
| 30.72 | 2.91 | 6330.00 | 20.11 |
| 31.45 | 2.84 | 4019.00 | 12.77 |
| 32.02 | 2.79 | 3494.00 | 11.10 |
| 32.98 | 2.72 | 6001.00 | 19.07 |
| 34.03 | 2.63 | 5111.00 | 16.24 |
| 35.90 | 2.50 | 4840.00 | 15.38 |
| 37.62 | 2.39 | 4396.00 | 13.97 |
| 39.48 | 2.28 | 6330.00 | 20.11 |
| 40.61 | 2.22 | 6176.00 | 19.62 |
| 41.05 | 2.20 | 6250.00 | 19.86 |
| 43.13 | 2.10 | 9371.00 | 29.77 |
| 45.28 | 2.00 | 5454.00 | 17.33 |
| 47.17 | 1.93 | 5973.00 | 18.98 |

| 2 theta | d/angström | Absolute intensity | Relative intensity/% |
|---|---|---|---|
| 48.14 | 1.89 | 5824.00 | 18.50 |
| 58.99 | 1.57 | 4621.00 | 14.68 |

The invention claimed is:

1. A compound of the formula (I)

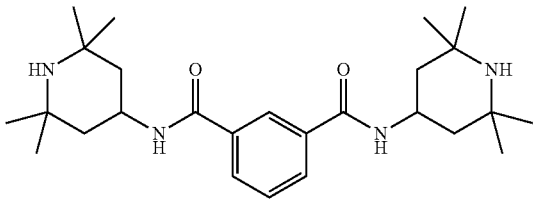

wherein an X-ray powder diffraction pattern of the compound has characteristic signals measured with Cu $K_{alpha}$ radiation at a 2-theta angle of 15.0 and 22.7 having a high intensity and of 5.0, 11.3, 18.9, 20.8, 21.6 and 23.6 having a moderate intensity.

2. A process for preparing the compound of the formula (I) as claimed in claim 1, comprising reacting at least one isophthalic diester of the formula (II)

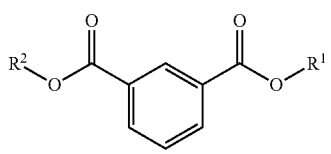

wherein $R^1$ and $R^2$ are the same or different and are an aliphatic radical, with 2 equivalents of 4-amino-2,2,6,6-tetramethylpiperidine in the presence of at least one catalyst, wherein the at least one catalyst is a metal alkoxide, at a reaction temperature between 50 and 150° C.

3. The process as claimed in claim 2, wherein the metal alkoxide is a compound of the formula (VI) and/or (VII)

$$X\text{---}OR^{13} \qquad (VI)$$

$$R^{14}O\text{---}Y\text{---}OR^{15} \qquad (VII)$$

wherein
$R^{14}$ and $R^{15}$ are each the same or different;
$R^{13}$, $R^{14}$ and $R^{15}$ are aliphatic radicals each having 1 to 20 carbon atoms;
X is an alkali metal; and
Y is an alkaline earth metal.

4. The process as claimed in claim 2, wherein the metal alkoxide is sodium methoxide, potassium methoxide, lithium methoxide, sodium ethoxide, potassium ethoxide, lithium ethoxide, sodium n-propoxide, potassium n-propoxide, sodium isopropoxide, potassium isopropoxide, sodium butoxide, potassium butoxide, sodium isobutoxide, potassium isobutoxide, sodium sec-butoxide, potassium sec-butoxide, sodium tert-amoxide, sodium amoxide, potassium amoxide, potassium tert-butoxide or a combination thereof.

5. The process as claimed in claim 2, wherein the metal alkoxide is added to the reaction mixture in amounts of 1 to 20 mol %, based on the isophthalic diester.

6. The process as claimed in claim 2, wherein the reaction is conducted solvent-free and in a reaction apparatus selected from the group consisting of mixers, kneaders and extruders.

7. The process as claimed in claim 6, wherein the reaction mixture, after the addition of the at least one catalyst, is mixed by the kneader, mixer or extruder at the reaction temperature for a period of 10 to 400 minutes.

8. The process as claimed in claim 6, wherein the kneader or mixer is equipped with sigma blades, masticator blades, plowshares, Becker blades, throwing paddles or a combination thereof.

9. The process as claimed in claim 2, wherein the isophthalic diester is dissolved in an excess of the 4-amino-2,2,6,6-tetramethylpiperidine.

10. The process as claimed in claim 2, wherein the isophthalic diester is dissolved together with two equivalents of the 4-amino-2,2,6,6-tetramethylpiperidine and a lipophilic liquid hydrocarbon or a mixture thereof.

11. The process as claimed in claim 2, wherein alcohol formed in the reaction is removed from the reaction mixture.

12. The process as claimed in claim 2, wherein the compound of the formula (I) precipitates out of the reaction mixture in solid form.

13. A polymer additive comprising a compound of the formula (I) as claimed in claim 1.

14. A stabilized polymer comprising a compound of the formula (I) as claimed in claim 1, wherein the stabilized polymer is stabilized against light and heat and has oxygen barrier properties.

15. The polymer additive as claimed in claim 13, wherein the polymer is selected from the group consisting of polyamides, polyesters and EVOH.

* * * * *